US00PP18506P2

(12) United States Plant Patent
Lim et al.

(10) Patent No.: US PP18,506 P2
(45) Date of Patent: Feb. 19, 2008

(54) GRANDIFLORA ROSE PLANT NAMED 'BAISME'

(50) Latin Name: *Rosa hybrida*
Varietal Denomination: BAIsme

(75) Inventors: Peter P. Lim, McMinnville, OR (US); Jerry Twomey, Leucadia, CA (US)

(73) Assignee: Bailey Nurseries, Inc., Newport, MN (US)

( * ) Notice: Subject to any disclaimer, the term of this patent is extended or adjusted under 35 U.S.C. 154(b) by 0 days.

(21) Appl. No.: 11/520,967

(22) Filed: Sep. 14, 2006

(51) Int. Cl.
*A01H 5/00* (2006.01)

(52) U.S. Cl. ..... Plt./136; Plt./130

(58) Field of Classification Search ..... Plt./136, Plt./130

See application file for complete search history.

*Primary Examiner*—Wendy Haas
(74) *Attorney, Agent, or Firm*—Penny J. Aguirre

(57) ABSTRACT

A new cultivar of grandiflora rose, *Rosa* 'BAIsme', characterized by its clusters of double flowers that are a blend of rosy-pink and apricot in color, its upright mounded plant habit, and its abundant flowers present in May and June and recurrently throughout the season over medium green, satiny, foliage that is resistant to rose blackspot and powdery mildew. The new variety is readily propagated on its own roots and hardy in U.S.D.A. Zones 5 to 9.

2 Drawing Sheets

Botanical classification: *Rosa hybrida.*
Variety denomination: 'BAIsme'.

BACKGROUND OF THE INVENTION

The present invention relates to a new and distinct cultivar of *Rosa hybrida.* The new cultivar will be referred to hereafter by its cultivar name, 'BAIsme'. 'BAIsme' is a grandiflora rose suitable for use in garden plantings.

The new cultivar of rose is a selection from a controlled breeding program conducted by the inventors in Yamhill, Oreg. with a focus to create cultivars of roses with greater winter hardiness and improvements in disease resistance combined with good flower quality.

The new variety of rose, 'BAIsme', designated as seedling No. 94G57, was selected among seedlings derived from a cross made in Yamhill, Oreg. in 1994 between the female parent, designated No. 4-219A (unnamed proprietary seedling, not patented) and the male parent, 'KORwest' (not patented). 'BAIsme' was selected as unique and budded onto understock in August 1995 and reselected by the inventors for its distinct characteristics in 1999.

The new cultivar has been asexually propagated by budding on an understock of 'Dr. Huey' (not patented) and by rooting of softwood cuttings. Asexual propagation in Yamhill, Oreg., St. Paul, Minn., and Litchfield, Ariz. by these techniques have determined that the characteristics of this cultivar are stable and are reproduced true to type in successive generations.

SUMMARY OF THE INVENTION

The following traits have been repeatedly observed and represent the characteristics of the new rose as observed for a period of five years in Yamhill, Oreg. and St. Paul, Minn. These attributes in combination distinguish 'BAIsme' as a unique cultivar of grandiflora rose.

1. 'BAIsme' exhibits clusters of double flowers that are a blend of rosy-pink and apricot in color. Flower color is classified as a pink-blend by American Rose Society standards.
2. 'BAIsme' has medium green foliage with a satin sheen.
3. 'BAIsme' exhibits an upright rounded plant habit.
4. 'BAIsme' is a recurrent bloomer, blooming abundantly in May and June and then recurrently throughout the season.
5. 'BAIsme' has shown excellent resistance to rose blackspot (*Diplocarpon rosae*) and powdery mildew (*Sphaerotheca pannosa* var. *rosa*).
6. 'BAIsme' is hardy in U.S.D.A. Zones 5 to 9.
7. 'BAIsme' is a vigorous grower and readily propagated by softwood cuttings and grown on its own roots.

The new cultivar of rose can be readily distinguished from its parents and other cultivars. The female parent, seedling No. 4-219A, a hybrid tea, has flowers that are deeper pink in color, exhibits a more upright plant habit, has lighter green foliage and is everblooming. The male parent, 'KORwest', a taller shrub rose, has flowers that are more apricot in color, darker green foliage, and is everblooming. The cultivars 'MEIpitac' (U.S. Plant Pat. No. 7,783) and 'AUSgrab' (not patented) are the closest comparison roses. They are both similar to 'BAIsme' in flower color, however they are both everblooming shrub roses and 'MELpitac' has flowers that are more pink in color with a compact rounded habit and 'AUSgrab' has fuller flowers that are more pink in color with a rounded plant habit.

BRIEF DESCRIPTION OF THE DRAWING

The accompanying colored photographs illustrated the overall appearance and distinct characteristics of the new rose, 'BAIsme', as grown outdoors in trail blocks and containers in St. Paul, Minn. and Yamhill, Oreg. The photographs were taken of two to three year-old plants grown own their own roots.

Figure 1:
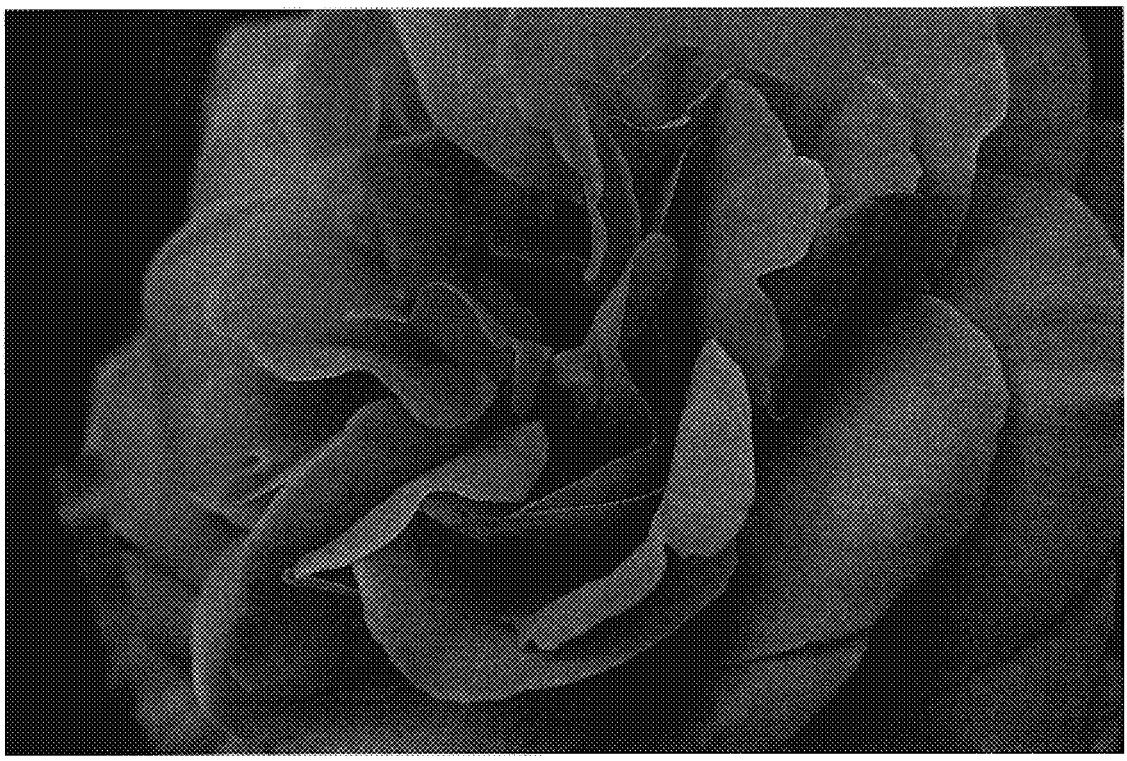
FIG. 1 provides a view of a fully open flower.
Figure 2:
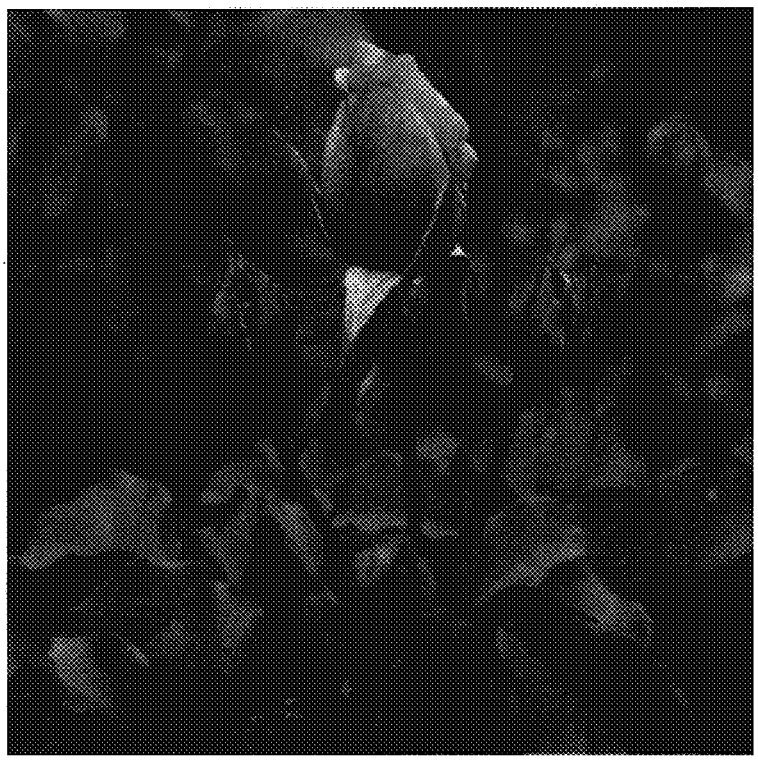
FIG. 2 provides a view a mature flower bud and foliage.
Figure 3:
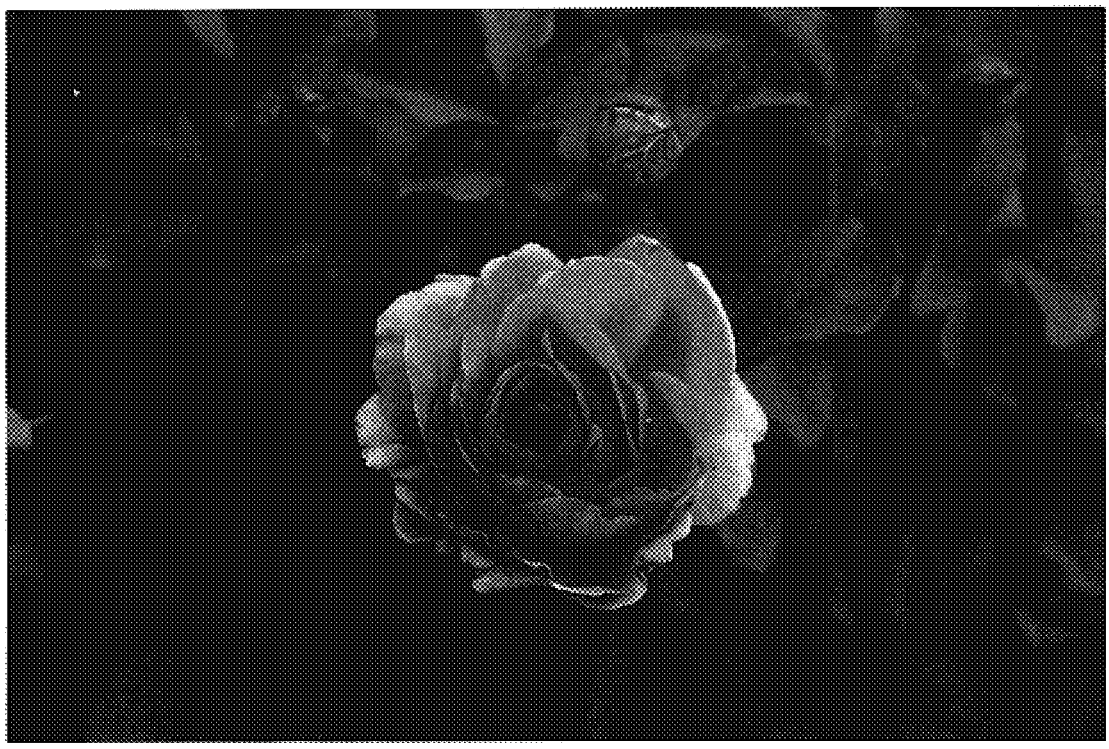
FIG. 3 provides a view of a flower just beginning to open.
Figure 4:
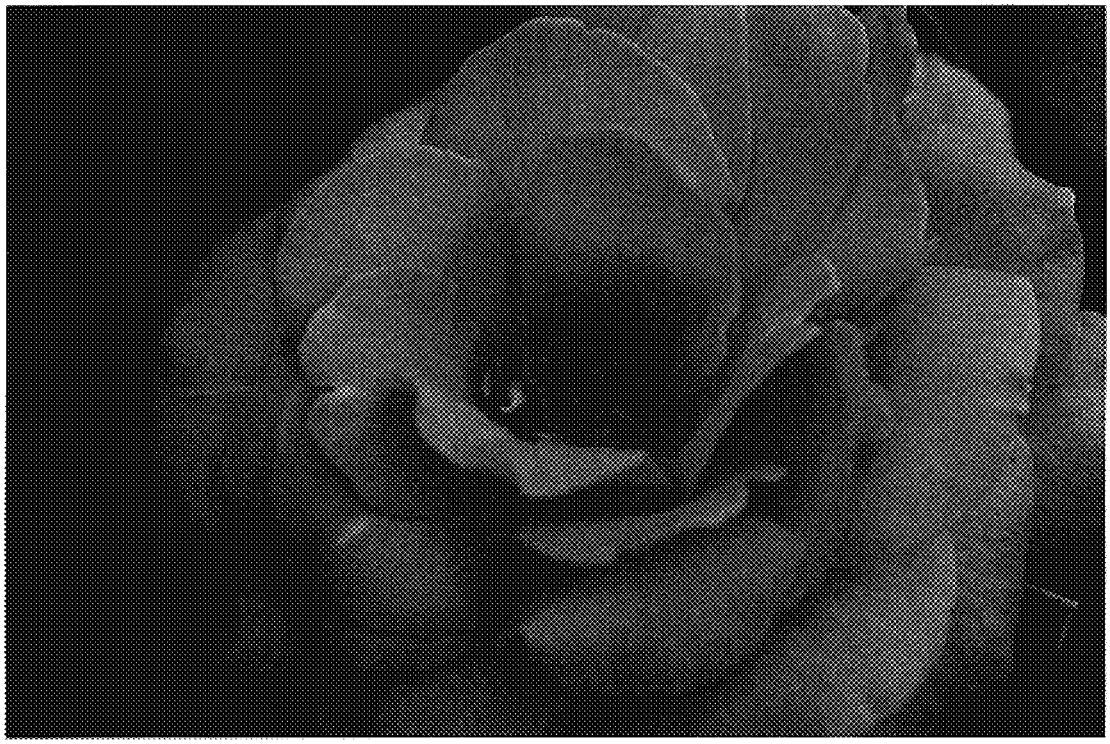
FIG. 4 provides a view of a mature flower.

The colors in the photographs are as close as possible with digital photography techniques available, the color values cited in the detailed botanical description accurately describe the colors of the new grandiflora rose.

DETAILED BOTANICAL DESCRIPTION

The following is a detailed description of the new cultivar as observed on two and three year-old plants grown outdoors under field conditions in Yamhill, Oreg., and St. Paul, Minn. The phenotype of the new cultivar may vary with variations in environmental, climatic, and cultural conditions, as it has not been tested under all possible environmental conditions. The color determination is in accordance with The R.H.S. Colour Chart of The Royal Horticultural Society, London, England, except where general color terms of ordinary dictionary significance are used.

General description:

*Botanical classification.*—*Rosa hybrida* 'BAIsme'.

*Parentage.*—Seed parent No. 4-219A (proprietary unnamed shrub rose seedling), pollen parent *Rosa* 'KORwest' (not patented).

*Blooming habit.*—Abundant in May and June and recurrent throughout the growing season.

*Plant habit.*—Upright rounded plant habit.

*Height and spread.*—Reaches 60 to 90 cm in height and 55 to 70 cm in spread.

*Cold hardiness.*—U.S.D.A. Zone 5 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young; 145A with slight blush of 185C, maturing; 147B, mature wood; 165A with some spots of 199A.

*Stem surface.*—Young; glabrous, adult wood; mostly glabrous with bark-like ridges and netting between.

*Thorns.*—Curved and slightly hooked in shape, canoe-shaped base, average of 4.2 per 5 cm in number, an average of 7 mm in length, color between 165A and 164A.

Foliage description:

*Leaves.*—Division is odd-pinnate, average of 11.75 cm in length and 9.15 cm in width, internode length is an average of 3.8 cm.

*Leaflets.*—Average of 5, oval to rotund in shape, rounded base, rounded to broadly acute apex, serrated margins, glabrous with satin sheen, average of 6.3 cm in length (ranges from 5.5 to 8 cm) and an average of 3.75 cm in width, color: young leaves upper surface: 187A, young leaves lower surface; 187B, mature leaves upper surface; between 147A and 147B, mature leaves lower surface; 147A.

*Rachis.*—Average of 4.75 cm in length and 4.6 mm in diameter, color of upper surface 146D with 145A between ridges with highlights of 185A, color of lower surface 145A.

*Stipules.*—Parallel with auricle facing outward, average of 4.25 cm in length and 3 mm in width, color of upper surface is 144B with 144A on ridges on either side of center ridge and suffused with 181B on center ridge and outer wings, color of lower surface 144B.

*Petioles.*—Average of 1.8 cm in length and 1.75 mm in diameter, glabrous surface, color of upper surface 146C with 145A between ridges and highlights of 185A, color of lower surface 145A.

Inflorescence description:

*Inflorescence type.*—Corymbs of double flowers.

*Flower number.*—Average of 3 per lateral stem.

*Flower fragrance.*—Spicy rose scent.

*Flower longevity.*—About 6 to 8 days, depending on temperature and sunlight exposure.

*Flower type.*—Double, imbricate.

*Flower size.*—Average of 10 cm in diameter and 3 cm in depth.

*Peduncles.*—Moderately stiff, average of 6.1 and 2.5 mm in diameter, surface has small flexible spines, color is 144B and 144C on upper and lower surface and suffused with 185A on upper side, covered with prickles of 183A.

*Flower buds.*—Globose to pointed, medium in size with an average of 2.3 cm in length and 1.6 cm in width prior to opening, color between 46C and 46D with 9A at the base petal spot, texture is glabrous to puberulent with some short hairs, mostly toward margins.

*Sepals.*—5, Lanceolate in shape, outer 3 sepals having 2 to 3 foliaceous appendages per side that are about 6.5 mm in length with an acute apex and a ciliate margin, inner sepals have entire margins with ciliate hairs, color of upper surface between 144A and 144B suffused with 185A and 185B, color of lower surface 147A, upper surface is satin to glossy with short hairs approaching the margin, lower surface is conescent with short hairs giving a white tint, average of 2.7 cm in length and 1 cm in width, apex is apiculate on 2 inner sepals and apiculate becoming leaf-like on the outer 3, base is truncate, aspect is upright in bud stage changing to horizontal when bud opens and reflexed in full bloom.

*Petals.*—20 to 25, drop readily and cleanly, broadly obovate in shape, upper and lower surface is glabrous and satiny, entire margin, cuneate base, rounded to truncate apex with some emarginate, average of 3.9 cm in length and 3.6 cm in width, color: opening flowers upper surface; 51A and 51B streaked with 47B and 6B toward base petal spot, opening flowers lower surface; 52B suffused with 52A toward margin and 6A and 6B toward base petal spot, fully open flowers upper surface; 48C with some streaking of 52A toward margin and 8B toward base petal spot, fully open flowers lower surface; between 16B and 16C with inner petals suffused with 22B, end of bloom upper surface; 51A and 51B with streaking of 52A toward margin and 8B toward base petal spot, end of bloom lower surface; 51C with streaking of 54C and 57D toward margin and suffused with 8B toward petal spot, base petal spot; 6B.

*Receptacle.*—When flower is fully open; average of 1.3 cm in diameter and 1.6 cm in depth, urn shaped, glabrous with some glaucous coating, color is between 143A with 184B on the side exposed to sun.

*Pistils.*—Average of 76, stigma is an average of 0.5 mm in length, an average of 0.8 mm in width and 47A in color, style is an average of 9 mm in length and 154A in color.

*Stamens.*—Average of 81, filaments are an average of 1.2 cm in length and 14A in color, anthers are an average of 2.2 mm in length, an average of 1 mm in width and 15D in color, pollen is 17B in color.

*Hips.*—Sparsely produced under the trial conditions, urn shaped, medium small in size with an average of 1.9 cm in length and 1.7 mm in diameter, surface is glabrous with some ridges, color is 146B suffused with 185B on the side expected to the sun, seeds; typically 4, rounded to oval in shape, an average of 5 mm in length and 4 mm in width, surface is rugose at apex with villose hairs, color is 166A with areas of 164A and 166D.

We claim:

1. A new and distinct cultivar of grandiflora rose plant named *Rosa* 'BAIsme' as herein illustrated and described.

* * * * *